US007481785B2

(12) United States Patent
Turrini et al.

(10) Patent No.: US 7,481,785 B2
(45) Date of Patent: Jan. 27, 2009

(54) ARTICULATED JOINT FOR KNEE BRACE

(75) Inventors: Alberto Turrini, Castel d'Azzano (IT); Moreno Ferrigolo, Dossobuono (IT)

(73) Assignee: F.G.P. SRL, Dossobuono (IT)

( * ) Notice: Subject to any disclaimer, the term of this patent is extended or adjusted under 35 U.S.C. 154(b) by 426 days.

(21) Appl. No.: 10/541,075

(22) PCT Filed: Oct. 22, 2004

(86) PCT No.: PCT/IT2004/000580

§ 371 (c)(1), (2), (4) Date: Jun. 29, 2005

(87) PCT Pub. No.: WO2005/041826

PCT Pub. Date: May 12, 2005

(65) Prior Publication Data

US 2006/0089580 A1 Apr. 27, 2006

(30) Foreign Application Priority Data

Oct. 31, 2003 (IT) .......................... VR2003A0128

(51) Int. Cl.
A61F 5/00 (2006.01)
A61F 5/37 (2006.01)
A61B 19/00 (2006.01)

(52) U.S. Cl. ................ 602/16; 602/5; 602/23; 602/26; 128/869; 128/870; 128/882

(58) Field of Classification Search ............ 602/5, 602/16, 23, 26, 41–44, 61–63; 128/861, 128/882, 869–870; 433/89
See application file for complete search history.

(56) References Cited

U.S. PATENT DOCUMENTS

| 4,372,298 A | 2/1983 | Lerman |
| 6,551,264 B1 | 4/2003 | Cawley et al. |
| 7,059,329 B2 * | 6/2006 | Mason et al. ............... 128/861 |
| 7,060,045 B2 * | 6/2006 | Mason et al. ............... 602/5 |

FOREIGN PATENT DOCUMENTS

WO  WO 93/22992  11/1993

OTHER PUBLICATIONS

International Search Report for International Application No. PCT/IT 2004/000580 Dated Mar. 16, 2005, 2 page(s).

* cited by examiner

Primary Examiner—Patricia M Bianco
Assistant Examiner—Brandon Jackson
(74) Attorney, Agent, or Firm—Greenberg Traurig, LLP

(57) ABSTRACT

An articulated joint (11) for a knee brace to control femoral-patellar instability comprises a central support bracket (10) designated to be fixed to the patella area in order to carry out angular movements dynamically following the two reciprocally articulated sectors it connects, comprising a pair of plates (18,19) which enclose the ends of the uprights (16,17). The second plate (19) is thicker than the first and comprises a second housing which passes transversally through the plate and is designed to accommodate the sliding cursor support (15) of the patellar bracket (10). The movements of the patellar bracket (10) are imparted by a specially shaped lever (24).

3 Claims, 3 Drawing Sheets

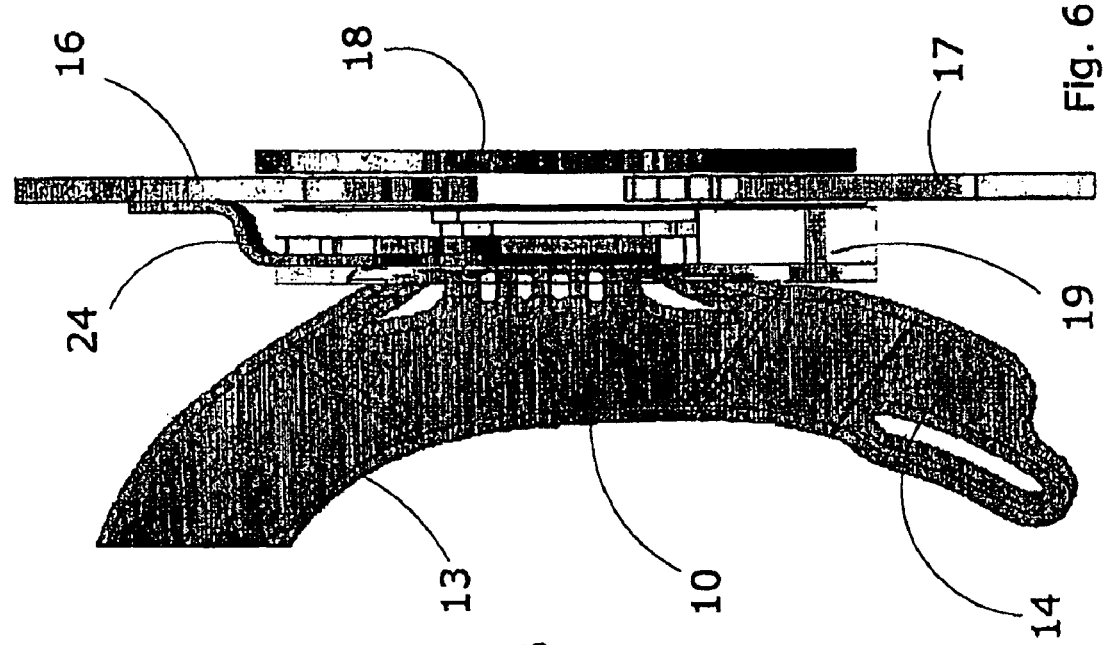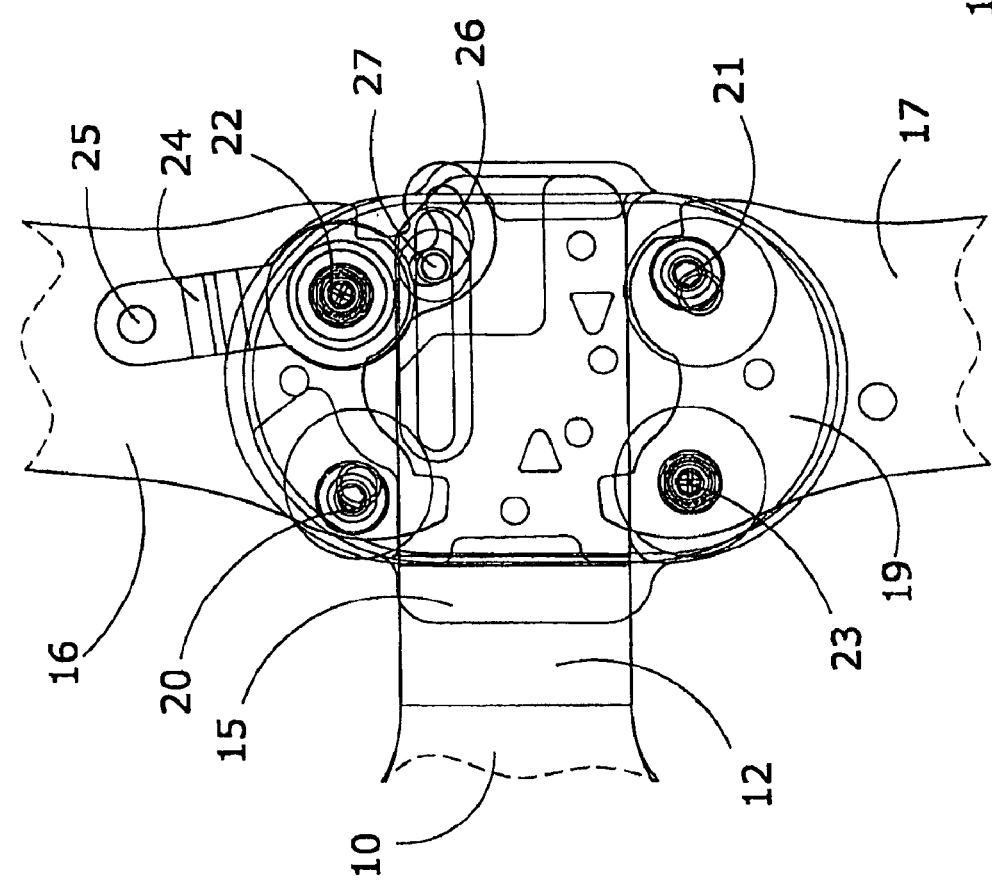

ARTICULATED JOINT FOR KNEE BRACE

This application is a national stage filing under 35 U.S.C. 371 of International Application PCT/IT2004/000580, filed on Oct. 22, 2004 which claims priority from Italian Application No: VR2003A000128, filed on Oct. 31, 2003. The entire teachings of the referenced Applications are incorporated herein by reference. International Application PCT/IT2004/000580, was published under PCT Article 21 (2) in English.

TECHNICAL FIELD

This invention concerns an articulated joint for a knee brace or orthopaedic walker, featuring the presence of particular means for controlling femoral-patella instability, in other words for making it possible to restrain the patella area and to follow its movement, respecting the dynamics of the anatomical movements of the patella.

More specifically, this invention concerns an articulated joint for a knee brace comprising a central support bracket designed to grip the patella area to allow the misaligned angular movements of the two reciprocally articulated sectors that it joins.

This allows the knee brace to follow the movement of the knee while remaining firmly in place, reducing the possibility of the brace moving and in particular of it slipping down.

The articulated joint according to the invention, which is part of a knee brace or walker that can be used in sports activities and post-operative rehabilitation, is aimed at making the movement of the knee easier, and in particular the sliding of the patella during the movement of the tibia with respect to the femur during walking or rehabilitation exercises.

This invention can be applied in the production of prostheses and walkers used mainly in conservative, post-trauma, rehabilitation and post-operative therapy.

BACKGROUND ART

It is known that in some disorders of the knee, and in particular during post-operative rehabilitation therapy following surgery involving the ligaments or other parts of the knee joint, it is necessary to use special knee braces or walkers that provide a certain degree of support to the still weak joint, absorbing the most intense stress.

Various types of knee braces are currently known and available, but in the majority of cases these consist of a rigid articulated frame, with a covering, padding and means for fixing to the leg.

All the components that make up the knee brace are constructed in such a way as to envelop the knee in order to ensure adequate support during walking, or in any case to guarantee the support of an impaired articulation.

The frames of traditional knee braces, rigid and articulated as stated above, comprise lateral uprights that are restrained by means of appropriate connections to the femoral and the tibial parts of the leg, and a connecting structure between these uprights consisting of a hinged joint at the level of the knee.

According to the most recent and advanced solutions, each of these hinged joints comprises pairs of pins that make up the same number of points of application and joints for the ends of the femoral and tibial uprights, in order to obtain a sufficiently mobile structure that allows sufficient articulation of the knee and at the same time a good level of stress resistance.

The known knee braces and walkers are normally equipped with straps or half-rings that permit the brace to be fixed close to the knee joint and blocked in the femoral and tibial areas.

The known articulated joints, which consist of pairs of pivots theoretically pre-arranged to allow correct movement of the limb, perform a certain extension outwards during flexion of the knee, while they tend to contract during extension of the knee, thus reducing the possibility of the knee brace moving and in particular of it slipping down.

There are also known articulated knee brace joints that are equipped with means that allow alteration of the configuration, in order to satisfy different requirements according to the size of the knee and to the type of mobility to be applied in the various cases and types of injuries or traumatic events.

The U.S. Pat. No. 6,551,264 in the name of Berg, Inc. foresees a knee brace equipped with a retaining sector that can be applied on the patella area.

According to this solution the rack end (156, 158) of the uprights (12, 14) positioned on the two hinges (156, 158) is connected to the double comb toothing (166) of a mobile bracket (162) that supports tension straps (78, 80), inserted in appropriate slots (110, 112) and designed to envelop the knee close to the patella.

The aim of this system is to fix the brace not only to the femoral and tibial areas but also to the patella area in order to accompany the movements of the brace during the flexion of the knee and to reduce the possibility of the brace moving from its position, preventing it in particular from slipping down.

It can nevertheless be noted that according to this solution the bracket (162) is positioned and moves in a substantially symmetrical and specular way with respect to the hypothetical median axis of the joint lying on the straight line equidistant between the two pins (152, 154) of the two uprights (12, 14).

This means a substantial limitation relative to the fact that from the anatomical point of view the patella does not move in a symmetrical and specular way with respect to the bisecting line of the knee joint, but slides in a misaligned way in its anatomical trochlear site.

It is in fact known that the knee is an extremely complex joint, subjected to forces that are exerted simultaneously on several planes, imposing considerable and diversified stress on the bone, capsular, meniscal, ligamentous and myotendinous structures.

In particular, the angular movement of the femoral-patella articulation of the knee is not exactly symmetrical and specular with respect to the hypothetical axis of symmetry between the femur and the tibia, but is more pronounced near the femoral part, which extends more during flexion.

The patella also slides in its site or trochlea during the bending of the joint, moving in its natural sliding plane, which is formed by the femoral groove, in a more pronounced way in the femoral part.

The disadvantage which has therefore been a common finding in all types of walkers and knee braces proposed to date on the market, and referring in particular to those equipped with bracket means that support the tension straps designed to envelop the knee close to the patella, is relative to the fact that the movement of the patella is not respected with this type of bracket.

In reality this drawback is due to the fact that the movement of the patella is not symmetrical with respect to the axis of symmetry between the femur and the tibia, and the known solutions do not foresee means that allow patellar brackets to follow the diversified movement of the patella that takes place between the tibial part and the femoral part.

This means that, even in the presence of bracket means designed to intervene in the patellar area to limit the possibility of the knee brace moving, a certain degree of slipping of the brace does take place, mainly downwards, since the symmetrical movement of the patellar bracket with respect to its sliding area does not correspond to the asymmetrical movement of the patella.

DESCRIPTION OF THE INVENTION

This invention proposes to provide an articulated joint for a knee brace that can eliminate or at least reduce the disadvantages described above.

In particular the articulated joint according to the invention proposes to remedy the drawbacks caused by the diversity and incompatibility between the symmetrical movement of the known patellar brackets with respect to the hypothetical axis of symmetry of the joint and the anatomically asymmetrical axis of the patella.

The invention also proposes to provide an articulated joint for a knee brace that can be easily produced in order to be economically advantageous as well as extremely efficient from the stability point of view.

This is due to the fact that the proposed aim is to produce a knee brace, of the type, equipped with patellar brackets, comprising means designed to follow the anatomical movement of the patella which is more pronounced in the femoral area, so as to prevent any possibility of the knee brace moving with respect to the knee joint on which it is mounted, preventing in particular the possibility of it slipping down.

This is achieved by means of an articulated joint for a knee brace with the features described in the main claim.

The dependent claims described advantageous embodiments of the invention.

The articulated joint for a knee brace according to the invention therefore foresees the presence of a femoral-patellar bracket which is applied, with the possibility of sliding and simultaneous controlled angular movement, on the knee brace joint.

This joint comprises a platform equipped with at least one pair of hinge fittings for respective uprights equipped with means of restraint to the femur and the tibia.

The platform presents a first shaped central plate, which may comprise a housing for interchangeable insert means, and a second shaped central plate, opposite the first plate, and which rests against the side of the knee. This second plate is thicker than the first and comprises a second housing which passes through the plate and is designed to accommodate the sliding-cursor support of the patellar bracket.

The ends of the femoral and tibial uprights are inserted between the first and second plate, so that they remain fixed in place.

The first shaped plate moves angularly in a different way with respect to the second shaped plate, since the first pin application points of the two femoral and tibial uprights are different from the second ones.

In particular, considering that the inner and outer sectors of the articulated joint and its components are those relative to the position of the patella with respect to the knee, the first plate is hinged on the outer sector of the end of the femoral upright and on the inner sector of the end of the tibial upright, while the second plate is hinged in a diametrically opposite way to the first, that is on the inner sector of the end of the femoral upright and on the outer sector of the end of the tibial upright.

The support cursor of the patellar bracket makes dynamic linear sliding movements in its housing in the second plate in order to move from a retracted position with the knee extended to an extended position with the knee flexed.

The dynamic linear sliding movements of the patellar bracket are imparted by a specially shaped lever which presents a rotation centre that corresponds to the one on which the second plate is mounted on the femoral upright, that is on the inner sector of its end. One end of this lever is hinged on the upright which provides its movement, while the other end is elbow-shaped and comprises a slot, also elbow-shaped, intercepted by a pin which is integral with the cursor of the patellar bracket.

The articulated joint is made from lightweight metal alloy or high-resistance composite plastic material, the surface resting against the limb being in any case made from anallergic material.

DESCRIPTION OF THE DRAWINGS

Other features and advantages of the invention will become evident on reading the following description of one embodiment of the invention, given as a non-binding example, with the help of the drawings shown in the attached pages, in which:

FIG. 5 shows a detailed partially transparent schematic view of the articulated joint from the inside;

FIG. 6 shows the detailed partially transparent schematic view of the articulated joint from the front;

DESCRIPTION OF ONE EMBODIMENT OF THE INVENTION

Figure 1:
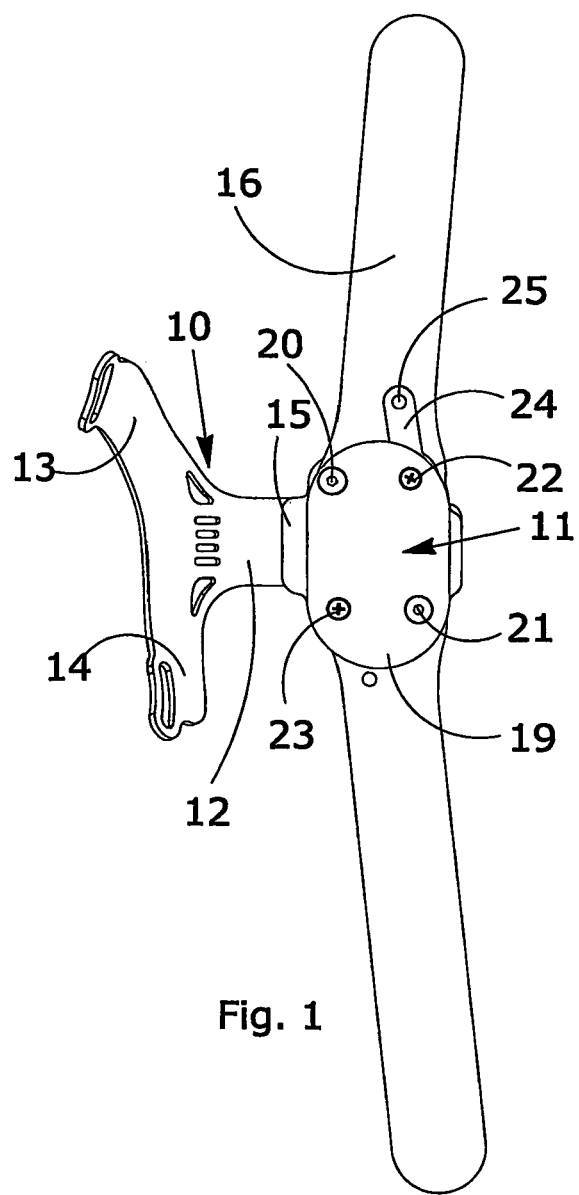
FIG. 1 represents a side schematic view of the articulated joint from the inner side, that is the side resting against the limb, in the fully extended position.
Figure 2:
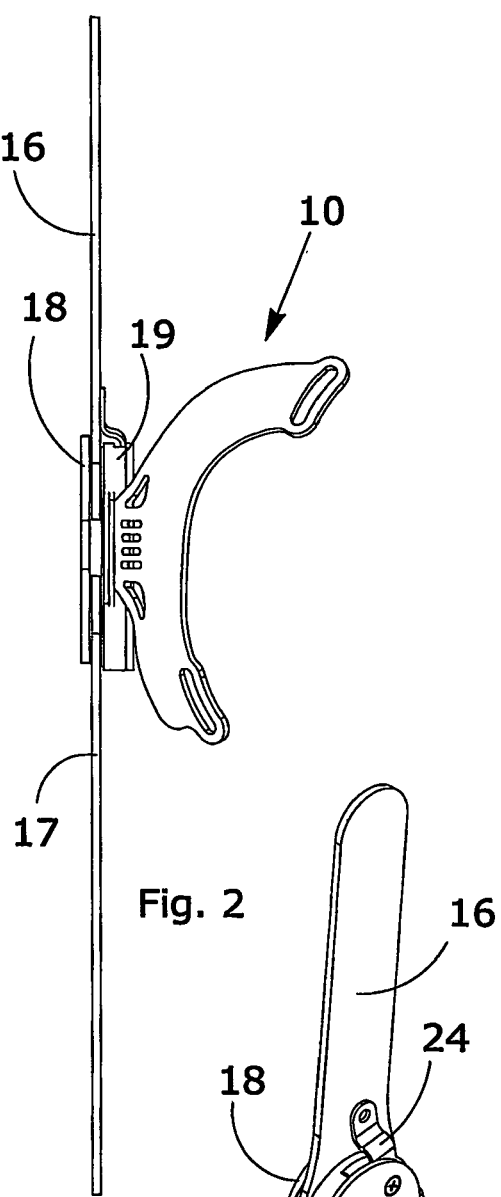
FIG. 2 shows a front view of the of the articulated joint from the patellar bracket side.
Figure 3:
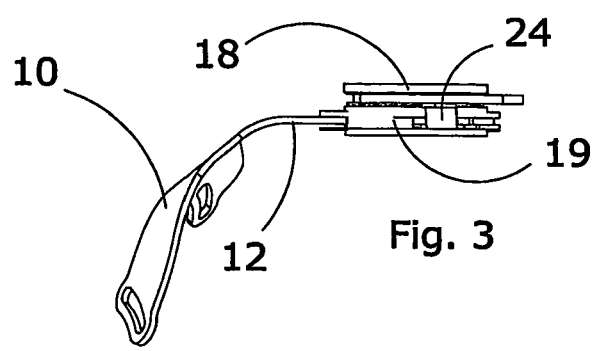
FIG. 3 shows a view of the articulated joint from above.
Figure 4:
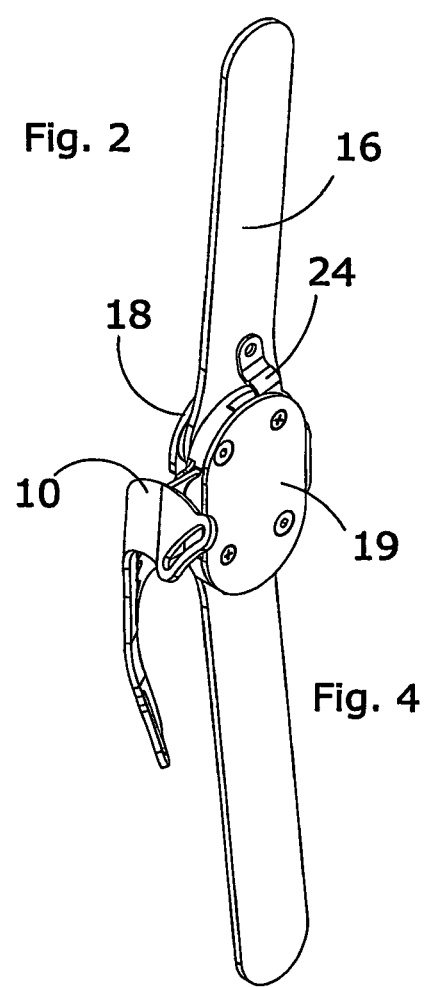
FIG. 4 is an axonometric view of the articulated joint from its inner three-quarters and slightly from above and in an extended position.

The knee brace articulated joint according to the invention foresees the presence of a patellar bracket 10 which is mounted, with the possibility of sliding and simultaneous controlled angular movement, on the knee brace articulated joint 11.

The patellar bracket 10 consists of a piece made from plastic material according to a conformation which presents a central portion 12 from which two arms 13 and 14 branch out, each comprising, at its end, a slot through which straps can be passed to fix the knee brace close to the patellar area of the knee.

The central portion 12 of the bracket is integral with a cursor 15, made from metal, which is inserted, with the possibility of sliding, in an appropriate housing inside the articulated joint 11, as will be better explained below.

This joint 11 consists of a platform equipped with at least one double pair of hinge fittings for the respective uprights 16 and 17, the first femoral and the second tibial, equipped with known means of restraint to the femur and the tibia.

The platform presents a first shaped central plate 18, which may comprise a housing for interchangeable insert means, and a second shaped central plate 19, which is opposite the first plate and rests against the side of the knee.

The second plate 19 is thicker than the first and comprises a second inner housing, which passes through it transversally, designed to accommodate the sliding cursor support 15 of the patellar bracket 10.

The ends of the femoral and tibial uprights 16 and 17 are inserted between the first plate 18 and the second 19, so that they remain fixed in place.

The first and the second plate 18 and 19 of the articulated joint 11 move angularly during flexion of the knee brace when the limb on which it is mounted is bent.

The first shaped plate 18 moves angularly in a different way with respect to the second shaped plate 19, since the first pin application points of the two femoral and tibial uprights are different from the second ones.

More specifically, considering that the inner and outer sectors of the articulated joint and its components are those relative to the position of the patella with respect to the knee, the first plate is hinged on the pin 20 on the outer sector of the end of the femoral upright 16 and on the pin 21 on the inner sector of the end of the tibial upright 17.

Vice versa the second plate 19 is hinged in a diametrically opposite way to the first, that is on the pin 22 on the inner sector of the end of the femoral upright 16 and on the pin 23 on the outer sector of the end of the tibial upright 17.

Figure 7:
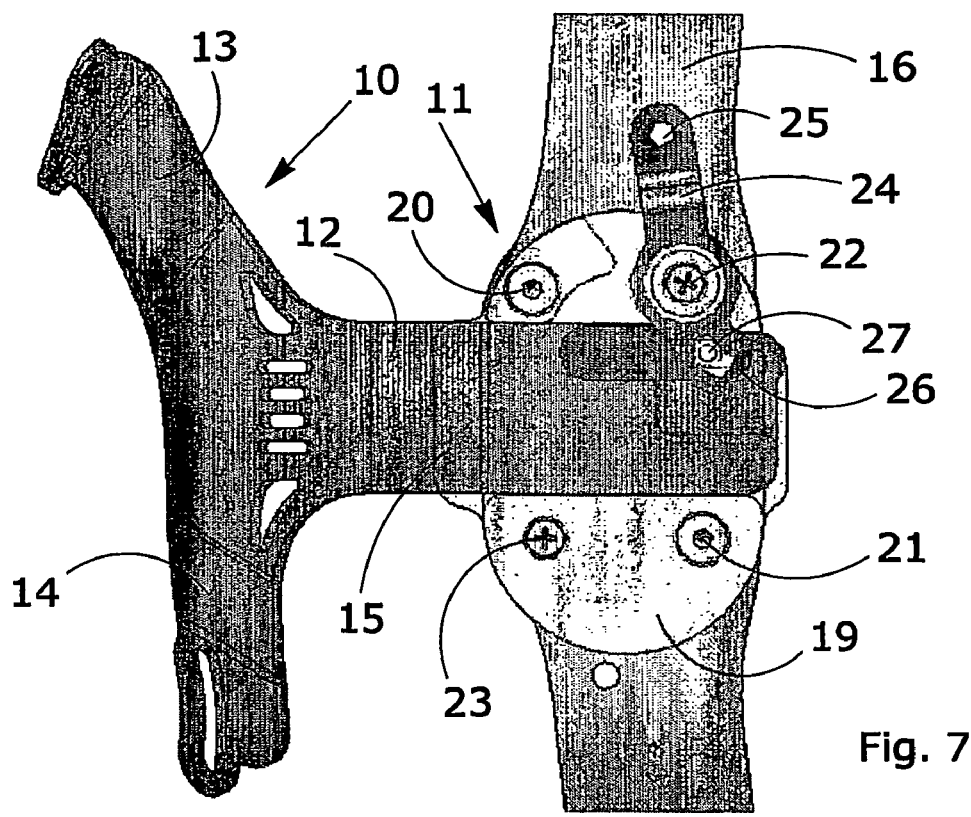
FIGS. 7 and 8 show axonometric side views of the articulated joint with a patellar bracket in a first and second operating phase.
Figure 8:
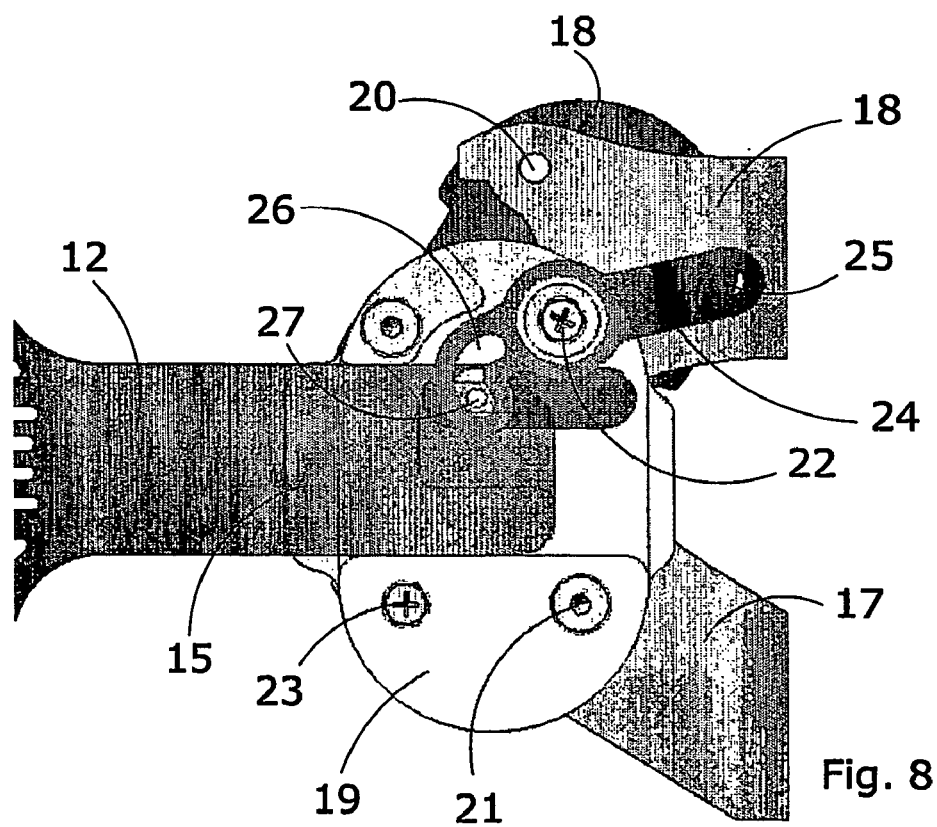

As shown in FIGS. 5, 7 and 8, the support cursor 15 of the patellar bracket 10 makes dynamic linear sliding movements in the transverse through housing in the second plate 19, in order to move from a retracted position with the knee extended (FIG. 7) to an extended position with the knee flexed (FIG. 8).

The dynamic linear sliding movements of the patellar bracket are imparted by a specially shaped lever 24 which presents a rotation centre that corresponds to the pin 22 on which the second plate 19 is mounted on the femoral upright 16, that is on the inner sector of its end.

The upper end of the lever 24 is hinged on the pin 25 on the upright 16 which provides its movement, while the other end, the lower end, is elbow-shaped, curved towards the inside of the knee brace, and comprises a slot 26 also elbow-shaped, intercepted by a pin 27 which is integral with the cursor 15 of the patellar bracket 10.

This conformation of the articulated joint allows the patellar bracket 10 to carry out a linear movement along its housing, driven by the lever 24. However, this movement is not symmetrical with respect to the hypothetical median line between the femoral upright and the tibial upright, but on the contrary the movement of the patellar bracket is more pronounced in the femoral sector area which moves more towards the tibial sector.

In particular, the movement of the patellar bracket angularly follows the movement of the inner plate 19 of the joint, which, as can be seen in FIG. 8, in the open position has a more pronounced angular movement towards the tibial upright with respect to the femoral upright.

While the patellar bracket moves outwards, it also performs an angular movement downwards, following the dynamics of the patella's sliding movement.

As mentioned above, the articulated joint is made from lightweight metal alloy or high-resistance composite plastic material, the surface resting against the limb being in any case made from anallergic material.

The invention is described above with reference to a preferred embodiment. It is nevertheless clear that the invention is susceptible to numerous variations within the framework of technical equivalents.

The invention claimed is:

1. An articulated joint for a knee brace to control femoral-patellar instability, comprising:
   a patellar bracket designed to be fixed to the patella area, the patellar bracket including a sliding cursor support;
   a first shaped central plate;
   a second shaped central plate opposite the first plate for resting against the side of the knee, the second plate being thicker than the first plate and having a housing passing transversally through the second plate, wherein the housing accommodates the sliding cursor support of the patellar bracket;
   a femoral upright having an end inserted between the first and second plate, wherein the second plate is hinged on a pin on an inner sector of the end of the femoral upright; and
   a specially shaped lever having an upper end and a lower end, the upper end of the lever being hinged on a rotation center corresponding to the pin on the femoral upright, the lower end elbow-shaped and curved towards the inside of the knee brace, the lower end including a slot also elbow-shaped, intercepted by a pin integral with the sliding cursor support of the patellar bracket.

2. An articulated joint for a knee brace to control femoral-patellar instability, comprising:
   a patellar bracket designed to be fixed to the patella area, the patellar bracket having a sliding cursor support;
   a femoral upright and a tibial upright, each having an inner sector and an outer sector;
   a first shaped central plate, the first plate being hinged on a first pin on the outer sector of an end of the femoral upright and on a second pin on the inner sector of an end of the tibial upright;
   a second shaped central plate opposite the first plate for resting against the side of the knee, the second plate being thicker than the first plate and being hinged on a third pin on the inner sector of the end of the femoral upright and on a fourth pin on the outer sector of the end of the tibial upright, the second plate also including a housing passing transversally through the second plate, wherein the housing accommodates the sliding cursor support of the patellar bracket; and
   a specially shaped lever having an upper end and a lower end, the upper end of the lever being is hinged on a rotation center corresponding to the third pin on the femoral upright, the lower end being elbow-shaped and curved towards the inside of the knee brace, the lower end including a slot also elbow-shaped, intercepted by a fifth pin integral with the sliding cursor support of the patellar bracket.

3. An articulated joint for a knee brace to control femoral-patellar instability, comprising:
   a patellar bracket designed to be fixed to the patella area, the patellar bracket having a sliding cursor support;
   a femoral upright and a tibial upright, each having an inner sector and an outer sector;
   a first shaped central plate;
   a second shaped central plate opposite the first plate for resting against the side of the knee, the second plate being thicker than the first plate and being hinged on a first pin on the inner sector of an end of the femoral upright and on a second pin on the outer sector of an end of the tibial upright, the second plate also including a housing passing transversally through the second plate, wherein the housing accommodates the sliding cursor support of the patellar bracket; and a specially shaped lever having an upper end and a lower end, the upper end of the lever being hinged on a rotation center corresponding to the first pin on the femoral upright, the lower end being elbow-shaped and curved towards the inside of the knee brace, the lower end including a slot also elbow-shaped, intercepted by a third pin integral with the sliding cursor support of the patellar bracket.

* * * * *